United States Patent [19]

Stadelhofer

[11] Patent Number: 5,408,225

[45] Date of Patent: Apr. 18, 1995

[54] MISALIGNMENT SENSING PROBE AND SWITCH

[76] Inventor: Eugene Stadelhofer, 46 S. Via Lucia, Alamo, Calif. 94507

[21] Appl. No.: 958,680

[22] Filed: Oct. 9, 1992

[51] Int. Cl.$^6$ ............................................. G08B 21/00
[52] U.S. Cl. ................................... 340/686; 340/635; 200/61.4; 417/63
[58] Field of Search ............... 340/679, 682, 686, 635; 384/624; 200/61.4, 61.41; 417/63

[56] References Cited

U.S. PATENT DOCUMENTS

| | | | |
|---|---|---|---|
| 3,897,116 | 7/1975 | Carpenter | 340/682 X |
| 4,584,865 | 4/1986 | Hutchins | 340/682 X |
| 5,140,311 | 8/1992 | Cook | 340/682 |

Primary Examiner—Jeffery A. Hofsass
Attorney, Agent, or Firm—Glen R. Grunewald

[57] ABSTRACT

A machine such as a centrifugal pump has a rotating impeller which may get out of alignment if there is bearing wear or if the impeller becomes loose on its supporting axle. A misalignment sensing probe and switch may be installed through the housing of the pump with it probe tip in close proximity to the impeller's face. If the rotating impeller migrates out of alignment it will abrade the tip of the sensing probe. Inside the probe body there is secured a stranded insulated electrical conductor with one of its ends in the tip while the other end extends beyond the other end of the body and is connected into an electrical circuit. Abrasion of the tip will force contact between the stranded electrical conductor wire and the body of the probe. This closing of the switch will activate the electrical circuit which has been designed to shut down the power source and/or activate an alarm and thus avoid destruction of the pump.

2 Claims, 2 Drawing Sheets

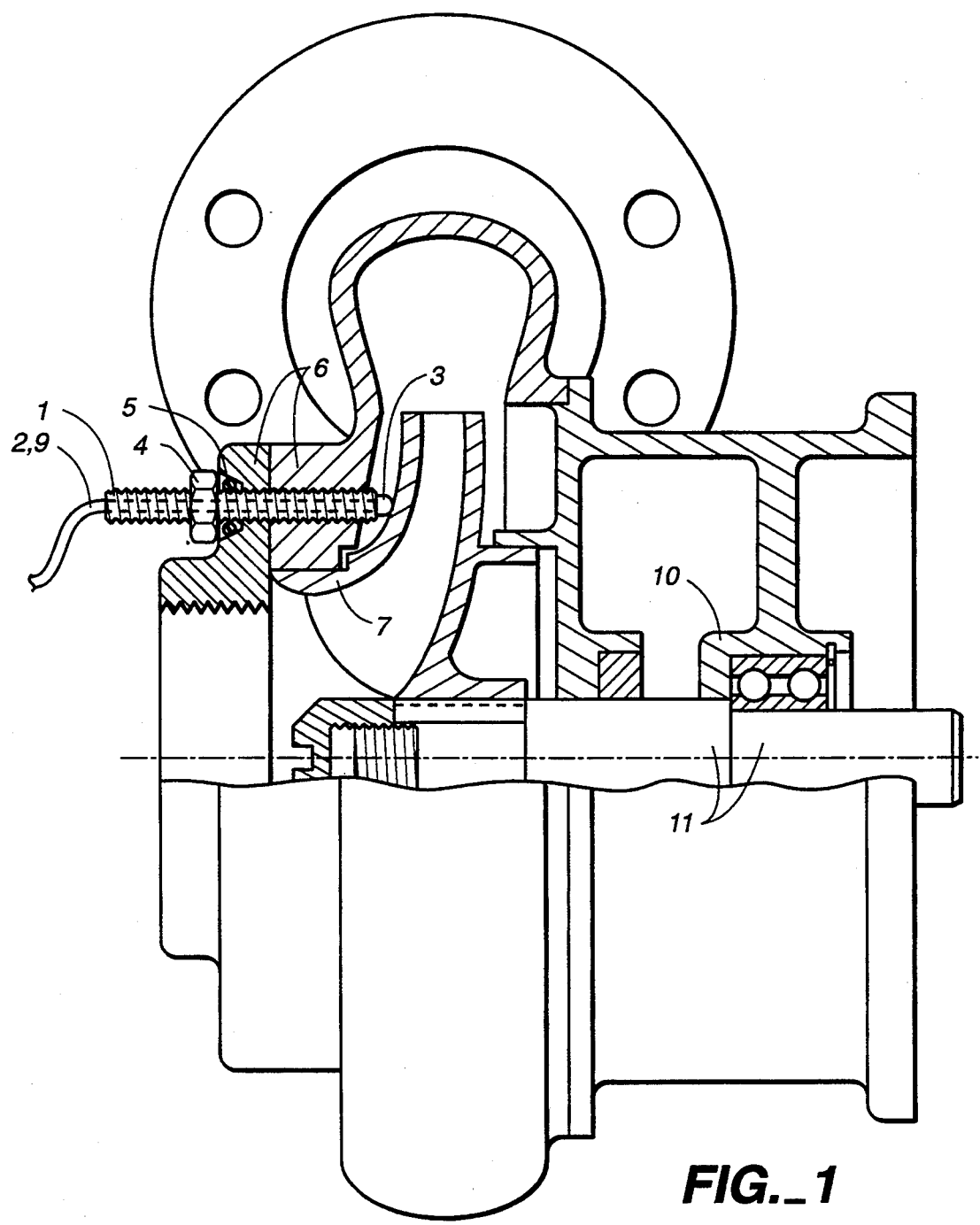
FIG._1

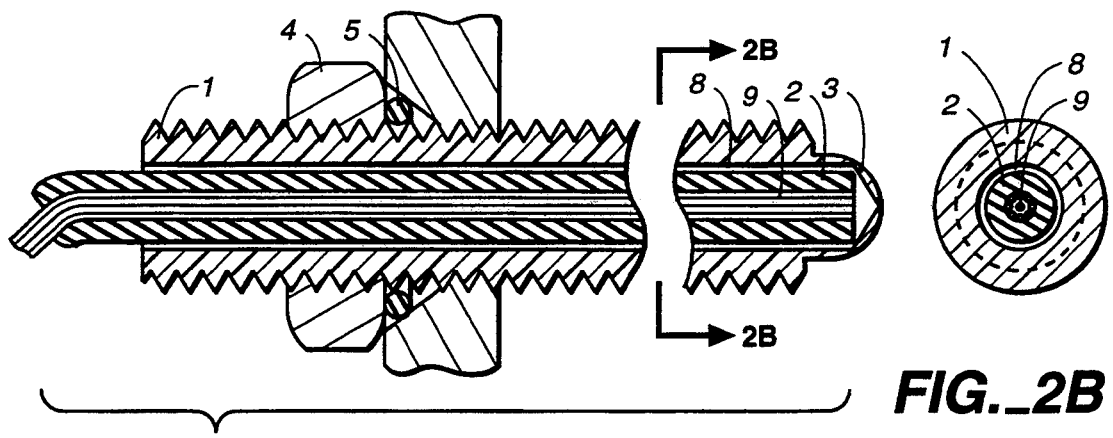
FIG._2A  FIG._2B
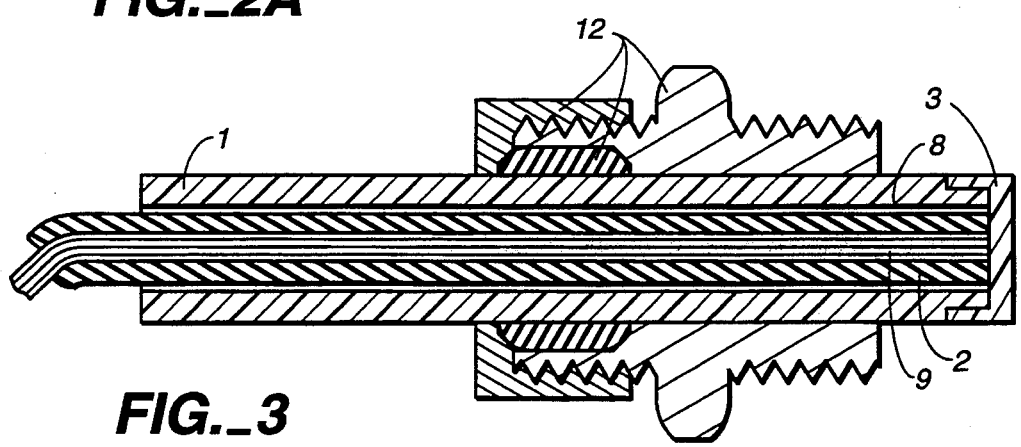
FIG._3
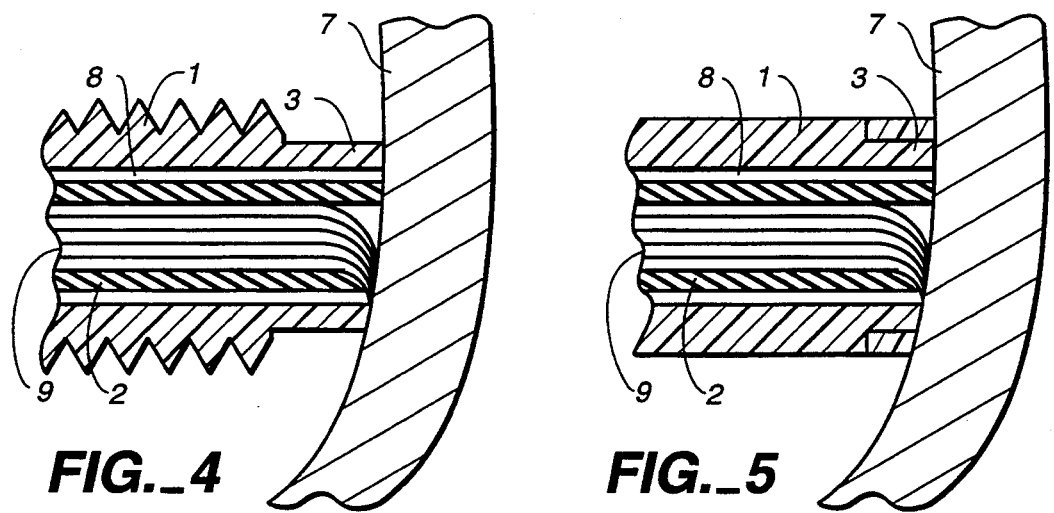
FIG._4  FIG._5

MISALIGNMENT SENSING PROBE AND SWITCH

BACKGROUND

The impeller in a centrifugal pump, turbine, or compressor can, as a result of either bearing wear or of becoming loose on its supporting axle, move axially out of alignment. The resulting misalignment can permit the rotating impeller to rub against the housing of said pump. If the driving power source continues to rotate said impeller the cumulative wear will quickly destroy both the impeller and the housing. A search has revealed no prior device or method for early detection of an impeller's displacement from its correct operational location.

ADVANTAGES

This inexpensive misalignment sensing probe with its normally nonconductive sensor switch in its tip can be installed to a proper depth by feel alone since said tip is not sensitive. An impeller rotating out of its proper alignment will abrade the probe tip closing the tip contained switch and activating a prearranged circuit which can shut down a power source and/or initiate a warning early enough to avoid destruction of costly equipment.

DRAWING FIGURES

FIG. 1 shows a typical installation of a misalignment sensing probe in the housing of a centrifugal pump with the probe tip location adjusted to be in close proximity to the impeller said misalignment sensing probe was installed to monitor.

FIG. 2A shows a cross sectional detail of a probe assembly including the internal insulated stranded copper conductor sealed inside with adhesive. The exterior of this version of the probe body is threaded to facilitate depth adjustment when it is inserted through a hole drilled and tapped in the sidewall of the pump housing. A lock nut secures said probe assembly's depth position while an O-ring provides a seal between the pump housing and said probe body. The tip end is enclosed with the same metal as said probe body.

FIG. 2B is a cross-section taken on the plane of the line 2B—2B shown in FIG. 2A.

FIG. 3 is an alternate probe body not having external threads. The interior cross section is the same as in FIG. 2 but a commercial ferrule type compression sleeve assembly is employed to facilitate setting the probe's depth and firmly securing its position in the pump assembly. The alternate tip enclosure illustrated is of plastic and not electrically conductive.

FIG. 4 shows the probe tip illustrated in FIG. 2 abraded to such an extent that the internal copper wires have been bent to make contact with the probe body and complete an electrical circuit.

FIG. 5 Shows the probe tip illustrated in FIG. 3 abraded to such an extent that the internal copper wires have been bent to make contact with the probe body and complete an electrical circuit.

Reference Numerals In Drawings

| | |
|---|---|
| 1 | Electrically conductive metal probe body |
| 2 | Insulating cover of stranded copper conductor |
| 3 | Sensing tip of probe |
| 4 | Lock nut |
| 5 | O-ring type washer |

-continued

Reference Numerals In Drawings

| | |
|---|---|
| 6 | Housing of pump |
| 7 | Impeller in pump |
| 8 | Adhesive securing insulated stranded wire in probe assembly |
| 9 | Electrical conductor composed of stranded copper wire |
| 10 | Bearings supporting axle |
| 11 | Axle |
| 12 | Commercial ferrule type compression sleeve |

DESCRIPTION

FIG. 1 Typical installation of a misalignment sensing probe in the housing 6 of a centrifugal pump. A mounting hole is drilled and tapped with female threads so the probe can be installed with its tip 3 close to the face of the impeller and near the outer circumference of said impeller 7. When being installed the probe is inserted until its sensing tip 3 is in contact with said impeller 7 and then it is retracted to provide proper clearance. Said misalignment sensing probe location is secured by lock nut 4 and sealed with respect to the housing 6 by O-ring 5.

FIG. 2 Cross sectional detail of the probe assembly wherein the threaded and hollow conductive metal probe body 1 has a stranded copper conductor 9 within an insulating cover 2 fastened in place with adhesive 8 so one end is just inside closed tip 3 but without contact between said conductor wire 9 and said probe body 1. The other end of the insulated 2 conductor wire 9 projects beyond the rear of said probe body 1 to connect with a prearranged electric circuit which can shut down power or provide a warning if ,said probe tip 3 is abraded sufficiently to serve as a switch closing said electric circuit.

FIG. 3 shows an alternate misalignment sensing probe and switch assembly which does not have. a threaded exterior. A standard commercial ferrule type compression sleeve 12 serves to clamp the cylindrical probe assembly in adjusted position. The hollow conductive metal probe body 1 has a stranded copper conductor 9 within an insulating cover 2 fastened in place with adhesive 8 so one end is just inside the alternate nonconductive plastic probe flip but without contact between said conductor wire 9 and said probe body 1. The other end of the insulated 2 conductor wire 9 projects beyond the rear of said probe body 1 to connect with a prearranged electric circuit which can shut down power or provide a warning if said probe tip 3 is abraded sufficiently to serve as a switch closing said electric circuit.

FIG. 4 Shows the shape of sensing probe tip 3 after an impeller 7, which has shifted laterally out of its correct operating position, has abraded away a portion of said probe tip 3 forcing the stranded copper wire 9 to bend and make contact with probe body 1. This contact permits the flow of an electric current in a circuit prearranged to shut down the power source and/or produce a warbling signal.

FIG. 5 Shows the alternate probe tip 3 illustrated in FIG. 3 after said plastic probe tip 3 has been sufficiently abraded to close an electrical circuit as described above for FIG. 4.

I claim:

1. A device to sense misalignment of an impeller rotating on a shaft in a housing comprising:

a hole through said housing opening adjacent said impeller;

a probe positioned in said hole, said probe including:
  a hollow electrically conductive body;
  an internal, deformable electrical conductor;
  insulation surrounding said deformable conductor to insulate it from said body; and
  an electrically insulating, abradable tip enclosing the end of said deformable conductor and the end of said insulation;

an open electric circuit including said deformable conductor, said body and means to detect misalignment;

whereby misalignment of said impeller causes abrasion of said tip and closes said open circuit by bringing said deformable conductor into contact with said body.

2. A probe useful to detect misalignment of an impeller rotating on a shaft in a housing, said probe comprising an electrically conductive body dimensioned to fit in a hole in said housing, an internal, deformable electrical conductor, insulation surrounding said deformable electrical conductor to insulate it from said body, an electrically insulating, abradable tip enclosing the end of said deformable conductor and the end of the insulation, and means to install said probe within said hole in said housing with said tip in close proximity to said impeller, whereby misalignment of said impeller causes abrasion of said tip and closes an open circuit by bringing said deformable conductor into contact with said body.

* * * * *